US00PP20000P2

(12) United States Plant Patent
Unger

(10) Patent No.: US PP20,000 P2
(45) Date of Patent: May 19, 2009

(54) ***CUPHEA* PLANT NAMED 'TRIPLE C'**

(50) Latin Name: *Cuphea ignea*
Varietal Denomination: Triple C

(76) Inventor: Christiaan Unger, Robert Koch Strasse 7, 67511 Worms (DE)

( * ) Notice: Subject to any disclaimer, the term of this patent is extended or adjusted under 35 U.S.C. 154(b) by 0 days.

(21) Appl. No.: 11/824,144

(22) Filed: Jun. 30, 2007

(51) Int. Cl.
*A01H 5/00* (2006.01)

(52) U.S. Cl. ..... Plt./420
(58) Field of Classification Search ..... Plt./420
See application file for complete search history.

(56) References Cited

U.S. PATENT DOCUMENTS

| | | | | | |
|---|---|---|---|---|---|
| PP5,214 | P | * | 4/1984 | Pottberg | Plt./226 |
| PP12,953 | P2 | * | 9/2002 | Rother | Plt./226 |
| PP13,595 | P3 | * | 2/2003 | Unger | Plt./226 |
| PP17,213 | P2 | * | 11/2006 | Keogh | Plt./425 |
| PP17,285 | P2 | * | 12/2006 | Keogh | Plt./420 |
| PP17,823 | P2 | * | 6/2007 | Keogh | Plt./420 |

* cited by examiner

*Primary Examiner*—Wendy C. Haas
(74) *Attorney, Agent, or Firm*—Mark P. Bourgeois

(57) ABSTRACT

A new and distinct *Cuphea* plant cultivar is disclosed, characterized by upright, mounding growth habit; dark green foliage; freely branching habit; and floriferous blooming of pink tubular flowers with yellow tips.

2 Drawing Sheets

Latin name of the genus and species: *Cuphea ignea.*
Variety denomination: 'TRIPLE C'.

BACKGROUND OF THE INVENTION

The new cultivar was discovered in October of 2002 by the inventor as a single plant growing in an outdoor garden of unnamed *Cuphea* cultivars in a cultivated area of Rheinfelden, Germany.

A sexual reproduction of the new cultivar 'TRIPLE C' by vegetative cuttings was performed in Oxnard, Calif. and has shown that the unique features of this cultivar are stable and reproduced true to type on successive generations.

SUMMARY OF THE INVENTION

The cultivar 'TRIPLE C' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TRIPLE C'. These characteristics in combination distinguish 'TRIPLE C' as a new and distinct *Cuphea* cultivar:

1. Upright, mounding growth habit;
2. Dark green foliage;
3. Freely branching habit; and
4. Floriferous blooming of pink tubular flowers with yellow tips.

Plants of the new cultivar 'TRIPLE C' differ from the unnamed *Cuphea* cultivars in the outdoor garden where 'TRIPLE C' was discovered primarily in flower color and branching habit. The unnamed *Cuphea* cultivars were orange with a broad branching habit.

In comparison to the commercially available variety 'Firecracker' (U.S. Plant Pat. No. 13,595), 'TRIPLE C' is taller and has a wider plant spread. Additionally, the new variety has darker foliage. Also, the flowers of 'TRIPLE C' stay in tubular form while the flowers of 'Firecracker' bloom further into an opened flower with obovate-shaped petals. Finally, the new variety 'TRIPLE C' has pink and yellow tubular flowers compared to the red and purple flowers of 'Firecracker.'

BRIEF DESCRIPTION OF THE PHOTOGRAPH

Figure 1:
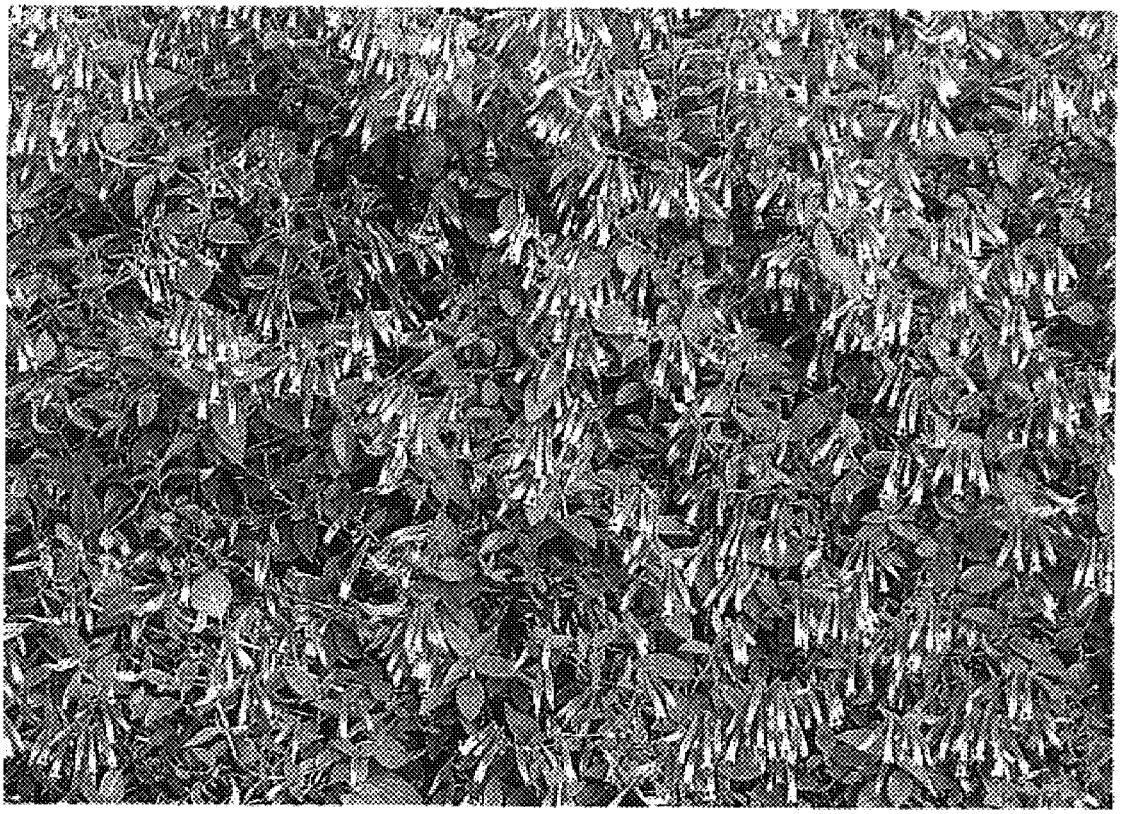

The accompanying photograph in FIG. 1 illustrates in close up view the flowers of 'TRIPLE C'.

Figure 2:
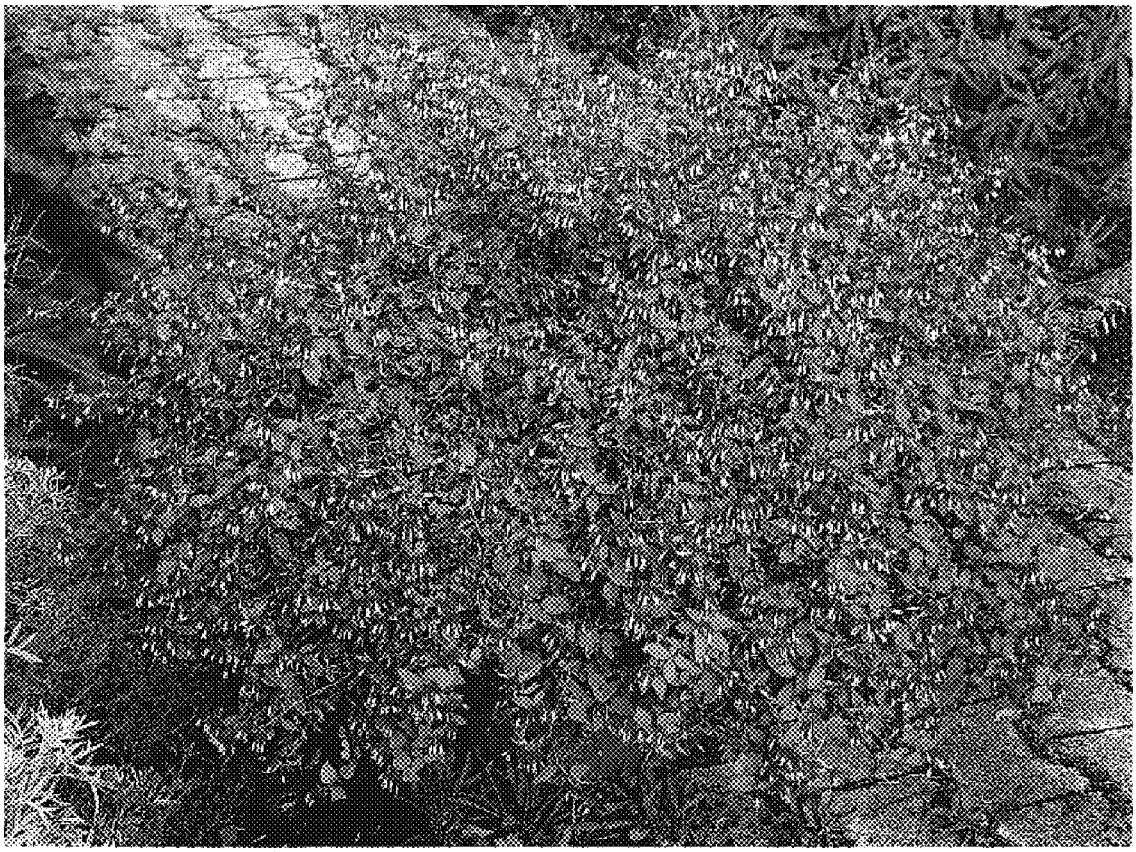

FIG. 2 is an overall photograph of the new cultivar in an outdoor garden. The colors are as nearly true as is reasonably possible in a color representative of this type.

DETAILED BOTANICAL DESCRIPTION

In the following description, color references are made to The Royal Horticultural Society Colour Chart except where general terms of ordinary dictionary significance are used. The following observations and measurements describe 'TRIPLE C' plants grown in Oxnard, Calif. during the months of January through June in an outdoor garden. The growing temperature ranged from 12° C. to 15° C. at night to 12° C. to 20° C. during the day. Measurements and numerical values represent averages of typical flowering types.

Botanical classification: *Cuphea ignea* cultivar 'TRIPLE C.'
Commercial classification: Cigar plant.

PROPAGATION

Time to rooting: 10 to 12 days at 22° C.
Root description: Broad.

PLANT

Growth habit: Upright, mounding herbaceous annual.
Height: Approximately 34 cm.
Plant spread: Approximately 72 cm.

Growth rate: Moderate.
Branching characteristics: Freely branching.
Internode length: Approximately 3 cm.
Age of plant described: Approximately 138 days.

FOLIAGE

Leaf:
*Arrangement.*—Opposite.
*Average length.*—Approximately 3.4 cm.
*Average width.*—Approximately 1.6 cm.
*Shape of blade.*—Lanceolate.
*Apex.*—Broadly acute.
*Base.*—Oblique.
*Attachment.*—Petiolate.
*Margin.*—Entire.
*Texture of top surface.*—Lightly pubescent.
*Texture of bottom surface.*—Lightly pubescent.
*Color.*—Young foliage upper side. Near Green 137C. Young foliage under side: Near Green 138B. Mature foliage upper side: Near Green 137B. Mature foliage under side: Near Green 138A.
*Venation.*—Type: Pinnate. Venation color upper side: Near Green 139C. Venation color under side: Near Green 137D.

Petiole:
*Average length.*—Approximately 1 cm.
*Color.*—Near Green 139C on upper side, near Green 137D on under side.
*Diameter.*—Approximately 0.1 cm.

FLOWER DESCRIPTION

Flower:
*Natural flowering season.*—Blooms almost continuously throughout the year.
*Flower type.*—Raceme.
*Flower number per branch.*—Approximately 56.
*Flower shape.*—Tubular.
*Flower size.*—Diameter: Approximately 0.5 cm. Length: Approximately 2.2 cm.
*Flower longevity.*—16 to 20 days.
*Persistence.*—Persistent, self-cleaning.
*Flower fragrance.*—None.

Flower bud:
*Length.*—Approximately 0.3 cm.
*Diameter.*—Approximately 0.1 cm.
*Form.*—Oblong.
*Color.*—Near Red-Purple 59C with shades of Yellow-Green 144C.

Corolla:
*Arrangement.*—Single fused tube of 6 petals.
*Petal texture.*—Rugulose.
*Petal margin.*—Entire.
*Petal apex.*—Obtuse.
*Petal Color.*—At first opening: Near Red-Purple 58C at base and near Yellow 2A at distal end. At maturity: Near Red-Purple 61D at base and near Yellow 6B at distal end. At fading: Near Red-Purple 63A at base and near Yellow 6A at distal end.

Peduncle:
*Length.*—Approximately 1.8 cm.
*Diameter.*—Approximate 0.1 cm.
*Strength.*—Moderate.
*Color.*—Near Yellow-Green 154C.

REPRODUCTIVE ORGANS

*Androecium.*—9.
*Stamens.*—Shortest Length: Approximately 0.2 cm. Longest Length: Approximately 0.6 cm. Texture: Glabrous. Color: Near Red-Purple 59B.
*Anthers.*—Length: About 1.5 mm. Color: Near Purple 79A.
*Pollen.*—None detected.
*Gynoecium.*—Number of pistils: 1. Pistil Length: Approximately 1.5 cm. Stigma Shape: Round. Stigma Color: Near Purple 79A. Style Color: Near Red-Purple 59A. Ovary Length: About 0.2 cm. Ovary Diameter: About 0.1 cm. Ovary Color: Near Yellow-Green 154D.

OTHER CHARACTERISTICS

Disease resistance: Neither resistance nor susceptibility to diseases or pests has been observed in this variety.
Drought tolerance cold tolerance: Moderate drought and cold tolerance.
Fruit/seed Production: Not observed because commercially the plants are discarded or the flowers removed before seed set occurs.

What is claimed is:

1. A new and distinct cultivar of *Cuphea* plant named 'TRIPLE C' as herein illustrated and described.

* * * * *